United States Patent [19]

Rubin et al.

[11] Patent Number: 4,870,163

[45] Date of Patent: Sep. 26, 1989

[54] PREPARATION OF PURE HUMAN TUMOR NECROSIS FACTOR AND HYBRIDOMAS PRODUCING MONOCLONAL ANTIBODIES TO HUMAN TUMOR NECROSIS FACTOR

[75] Inventors: Berish Y. Rubin, Brooklyn; Sylvia L. Anderson, New York; Susan A. Sullivan, Brooklyn; Lloyd J. Old, New York, all of N.Y.; Barbara D. Williamson, Old Greenwich, Conn.; Elizabeth C. Richards, Tarrytown, N.Y.

[73] Assignees: New York Blood Center, Inc.; Sloan-Kettering Institute for Cancer Research, both of New York, N.Y.

[21] Appl. No.: 770,808

[22] Filed: Aug. 29, 1985

[51] Int. Cl.$^4$ .................... C07K 3/12; C07K 3/18; C07K 3/20
[52] U.S. Cl. ................... 530/413; 530/395; 530/415; 530/829; 435/7; 435/172.2; 435/240.27; 436/548
[58] Field of Search ............... 530/351, 395, 413, 415, 530/829; 514/2; 424/95; 435/7, 68; 436/548, 811, 813; 935/12, 100

[56] References Cited

U.S. PATENT DOCUMENTS

| | | |
|---|---|---|
| 4,309,418 | 1/1982 | Green . |
| 4,444,744 | 4/1984 | Goldenberg .................. 424/1.1 |
| 4,447,355 | 5/1984 | Sakamoto et al. . |
| 4,495,282 | 1/1984 | Ohnishi et al. . |
| 4,503,035 | 3/1985 | Pestka ........................ 424/85 |
| 4,614,651 | 9/1986 | Jarvis et al. .................. 424/85 |
| 4,650,674 | 3/1987 | Aggarwal et al. .............. 514/12 |
| 4,677,064 | 6/1987 | Mark et al. ................... 435/253 |
| 4,778,879 | 10/1988 | Mertelsmann et al. ......... 530/351 |

FOREIGN PATENT DOCUMENTS

| | | |
|---|---|---|
| 0168214 | 1/1986 | European Pat. Off. . |
| 0183198 | 6/1986 | European Pat. Off. . |
| 3421731 | 12/1985 | Fed. Rep. of Germany . |

OTHER PUBLICATIONS

Proc. Natl. Acad. Sci. USA, Williamson et al, vol. 80, pp. 5397-5401, 9/1983.
Green et al, Proc. Nat. Acad. Sci. USA, vol. 73, 1976, pp. 381-385.
Ruff et al, The Journal of Immunology, vol. 125, 1980, pp. 1671-1677.
Mannel et al, Infection and Immunity, vol. 30, 1980, pp. 523-530.
Chemical Abstracts, 105, 1986, 105:207220d, "An Enzyme-Linked Immunosorbent Assay for Recombinant Human Tumor Necrosis Factor Using Monoclonal Antibody", p. 451.
J. of Biological Chemistry, vol. 260, Issue of 2/25/85, pp. 2345-2354, Aggarwal et al.
Chemical Abstracts, vol. 105, No. 11, 9/15/86, p. 493, Abstract 95800j.
Columbus, OH, US, B. Y. Rubin et al: "Human Tumor Recrosis Factor (LuKII): Recent Developments".
(List continued on next page.)

Primary Examiner—Esther M. Kepplinger
Assistant Examiner—Florina B. Hoffer
Attorney, Agent, or Firm—Sprung Horn Kramer & Woods

[57] ABSTRACT

Human TNF(LuKII) having a specific activity of at least $1.5 \times 10^5$ units per milligram of total protein is produced by contacting a TNF-containing protein composition, which has been harvested from human cell lines of hematopoietic origin or recombinant origin, in separate adsorption stages with glass beads, lentil lectin bound to Sepharose, and procion red agarose, thereby selectively to adsorb TNF in each stage, while leaving some impurities unadsorbed, each contact stage being followed by contact of the adsorbent with an eluant thereby to obtain a solution of more highly purified TNF after each stage. The purified human TNF(LuKII) is used to produce monoclonal antibodies against TNF(LuKII) and such antibodies can be used to assay samples for the presence of TNF(LuKII).

2 Claims, 4 Drawing Sheets

OTHER PUBLICATIONS

Chemical Abstracts, vol. 104, 1986, 86989e, "Monoclonal Antibody to Human Tumor Necrosis Factor", p. 534.

*Proc. Natl. Acad. Sci. USA*, 82, pp. 6637–6641, 10/85, "Purification and Charac. of a Human Tumor Necrosis Factor from the LuKII Cell Line", Rubin et al.

Aggarwal et al, "Human Lymphotoxin", *The Journal of Biological Chemistry*, vol. 259, Jan. 10, 1984, pp. 686–691.

J. Cell Biology, 79, 67 (1978), to Green et al.

Cancer Letters, 6, 235–240 (1979) to Green et al.

Cancer Letters, 11, 345–350 (1981) to Green et al.

Williams et al, J. Immunology, 130, 518–520 (1983).

AACR Abstracts, p. 211, No. 831 (1983) to Khan et al.

E. A. Carswell et al, Proc. Natl. Acad. Sci. USA, 72, 3666–3670, (1975).

L. Helson, et al, Nature (London) 258, 731–732 (1975).

D. N. Mannel et al, Infect. Immun., 28, 204–211 (1980).

F. C. Kull and P. Cuatrecasas, J. Immunol., 126, 1279–1283 (1981).

K. Haranaka and N. Satomi, Jpn. J. Exp. Med., 51, 191–194 (1981).

N. Matthews and J. F. Watkins, Br. J. Cancer, 38, 302–309, 310–315 (1978).

J. M. Ostrove and G. E. Gifford, Proc. Soc. Exp. Biol. Med., 160, 354–358 (1979).

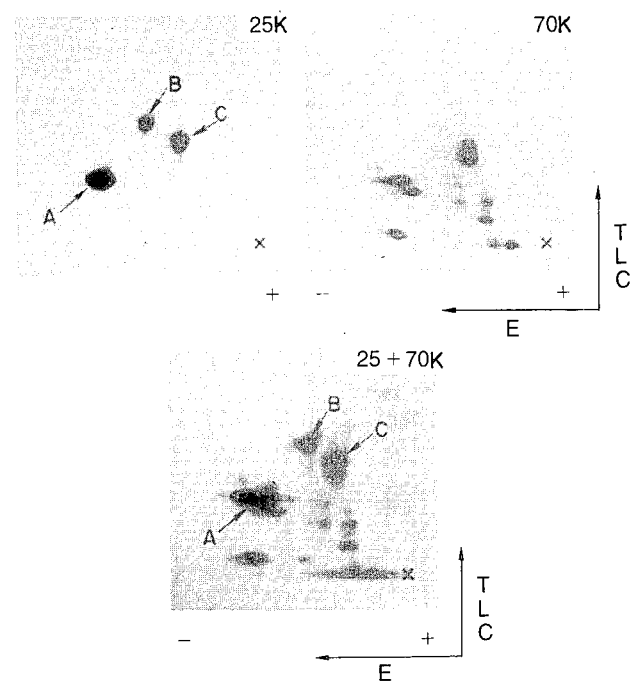
$M_r \times 10^{-3}$
43 —
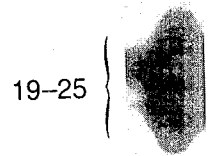
19–25
FIG. 7

PREPARATION OF PURE HUMAN TUMOR NECROSIS FACTOR AND HYBRIDOMAS PRODUCING MONOCLONAL ANTIBODIES TO HUMAN TUMOR NECROSIS FACTOR

BACKGROUND OF THE INVENTION

The present invention relates to a sequential chromatographic procedure for the purification of a human tumor necrosis factor, produced, by the LuKII cell line, termed TNF(LuKII), the characterization of TNF(LuKII) and hybridoma cell lines producing monoclonal antibodies to TNF(LuKII).

It has been reported that during certain bacterial infections, for example, staphylococcal and streptococcal, there sometimes occurs a concomittant regression of human tumors.

Coley and others treated human malignancies with heat-killed bacterial vaccines and obtained positive results in some patients.

The presence of a tumor inhibitory factor in the sera of mice infected with bacillus Calmette-Guerin (BCG) and subsequently injected with endotoxin was reported by E. A. Carswell et al, *Proc. Natl. Acad. Sci. U.S.A.*, 72, 3666–3670 (1975). This sera has been observed to cause the hemorrhagic necrosis and regression of certain mouse tumors in vivo. This sera was also found to have cytotoxic/cytostatic effects on mouse and human tumor cells in vitro (E. A. Carswell et al, supra; L. Helson, et al, *Nature* (London), 258, 731–732 (1975); D. N. Mannel et al, *Infect. Immun.*, 28, 204–211 (1980); F. C. Kull and P. Cuatrecasas, *J. Immunol.*, 126, 1279–1283 (1981); K. Haranaka and N. Satomi, *Jpn. J. Exp. Med.*, 51, 191–194 (1981)). A similar factor was found to be induced in rats (Carswell et al, supra) and rabbits (Carswell et al, supra; N. Matthews and J. F Watkins, *Br. J. Cancer*, 38, 302–309 (1978); J. M. Ostrove and G. E. Gifford, *Proc. Soc. Exp. Biol. Med.*, 160, 354–358 (1979)).

The antitumor factor present in the sera of animals sensitized to BCG or other immunopotentiating agents, such as *Corynebacterium parvum*, Malaria or Zymosan (yeast cell wall), and then challenged with endotoxin has been termed tumor necrosis factor (TNF).

Biochemical studies have indicated that mouse serum TNF is a glycoprotein and that its activity is associated with both high molecular weight components, e.g., $M_r$ 150,000, (Kull and Cuatrecasas, supra and S. Green et al, *Proc. Natl. Acad. Sci U.S.A.*, 73, 381–385 (1976)) and components in the $M_r$ 40,000–60,000 range, (D. N. Mannel et al, supra; Kull and Cuatrecasas, supra; and Haranaka, supra). The molecule is stable when frozen, preferably below $-70°$ C. Its activity is destroyed at $70°$ C. for 30 minutes. It is pyrogenic in rabbits in a range from 5–500 microgram/kg and non-pyrogenic at 5 microgram/kg. TNF in rabbit serum has also been reported to have a molecular weight of 39,000, (N. Matthews et al, *Br. J. Cancer*, 42, 416–422 (1980)), and 67,000, (M. R. Ruff and G. E. Gifford, *J. Immunol.*, 125, 1671–1677 (1980)).

Studies have indicated that both in vivo and in vitro activities of mouse TNF appear to be a property of the same molecule. The cellular source of TNF in the mouse was initially assumed to be the macrophage, because the agents used to prime for TNF production cause massive hyperplasia of macrophages in liver and spleen (Carswell et al, supra). From studies of macrophage-rich cell populations in vitro, (N. Matthews, *Br. J. Cancer*, 38, 310–315 (1978) and D. N. Mannel et al, *Infect. Immun.*, 30, 523–530 (1980)) a similar conclusion was reached with regard to the source of mouse and rabbit TNF. Direct evidence that macrophages are at least one cell type in the mouse capable of producing TNF comes from studies with cloned lines of mouse histiocytomas (D. N. Mannel et al, supra and unpublished data). These cells constitutively produce low levels of TNF that are greatly increased after exposure to endotoxin.

B. D. Williamson et al, *Proc. Natl. Acad. Sci. U.S.A.*, 80, 5397–5401 (1983), described the capacity of human cell lines of hematopoietic origin, e.g., B-cell lines, to produce a factor with TNF activity. The product of one of the B-cell lines (LuKII) was chosen for detailed studies. Evidence demonstrating that this molecule is a human TNF included the following: (1) the anticellular response of a panel of human cell lines to human TNF, e.g., TNF(LuKII), or mouse TNF are indistinguishable and can be potentiated in a synergistic fashion by interferon, (2) mouse L cells made resistant to mouse TNF are resistant to human TNF, e.g., TNF (LuKII), (3) mouse L cells made resistant to human TNF, e.g., TNF(LuKII) are resistant to mouse TNF, and (4) human TNF, e.g., TNF(LuKII), causes hemorrhagic necrosis of Method A sarcoma in the standard in vivo TNF assay, B. D. Williamson, supra.

Heretofore, there have been no known purification methodologies to obtain pure TNF(LuKII) which are rapid and efficient, for example, which do not require dialysis which may involve serious losses of material. At the present time there is also no hybridoma in existence which produces a monoclonal antibody to the pure TNF(LuKII), which would be extremely useful for purification, diagnostic, and perhaps therapeutic purposes.

SUMMARY OF THE INVENTION

It is accordingly an object of the present invention to provide a process for the purification of TNF(LuKII) which yields both good recoveries of TNF activity and high specific activity material. The pure TNF(LuKII) can be used therapeutically.

It is another object of the present invention to isolate this TNF(LuKII) in a form suitable for producing hybridoma cell lines which produce monoclonal antibodies to TNF(LuKII), to allow for the rapid purification and detecting of the presence of TNF(LuKII) for diagnostic purposes.

This and other objects and advantages are realized in accordance with the present invention pursuant to which a purified TNF(LuKII), i.e., a human TNF having an activity of at least $1.5 \times 10^5$ units per milligram of total protein is obtained by contacting a TNF-containing protein composition, which has been harvested from human cell lines (e.g., human cell lines of hematopoietic origin, particularly B-cell lines such as the LuKII cell line) or produced by recombinant technologies, in separate adsorption stages with glass beads, lentil lectin bound to Sepharose, and procion red agarose, thereby selectively to adsorb TNF in each stage while leaving some impurities unadsorbed, each contact stage being followed by contact of the adsorbent with an eluant thereby to obtain a solution of more highly purified TNF after each stage. In a preferred process for obtaining purified TNF, the glass beads are the first stage adsorbent, the Sepharose-bound lentil lectin is the second stage adsorbent and the procion red agarose is the third stage adsorbent.

The purification process of the present invention allows the TNF(LuKII) eluted from one column to be applied, either directly or after dilution, onto the next column, thereby eliminating any need for dialysis and thus avoiding the losses associated with dialysis.

The TNF which is purified to obtain the TNF of the invention can be harvested from human cell lines of hematopoietic origin, particularly B-cell lines. Recombinant methodologies can also be used to produce a TNF-containing composition. For example, the gene responsible for TNF(LuKII) production can be implanted in *E.coli* which, in turn, produce TNF(LuKII) in large quantities. The recombinant techniques used are known (e.g., T. Maniatis et al, *Molecular Cloning*, Cold Spring Harbor Laboratory, 1982).

The purified TNF(LuKII) of the invention comprises a plurality of fractions of protein molecules of different molecular weights, each of which, it is believed, has TNF activity. More particularly, the TNF(LuKII) comprises at least three fractions. Even more particularly, the TNF(LuKII) comprises seven fractions, each of which, it is believed, has TNF activity.

The purified TNF(LuKII) of the invention may have different numbers of protein fractions, each fraction having a different molecular weight. For example, the TNF(LuKII) of the invention may have two fractions, for example, corresponding to the molecular weights of, for example, 70,000 and 25,000 daltons, respectively; or, the TNF(LuKII) of the invention may have three fractions, for example, corresponding to the molecular weights of, for example, 70,000, 25,000 and 19,000 daltons, respectively; or the TNF(LuKII) of the invention may have seven fractions corresponding to the molecular weights of 80,000; 70,000; 43,000; 25,000; 23,000; 21,000; and 19,000 daltons, respectively.

The TNF(LuKII) of the invention is further characterized in having a specific activity of at least $1.5 \times 10^5$ units per milligram of total protein, e.g., $1.5 \times 10^5$ to $1.5 \times 10^8$ units per milligram of total protein, more particularly, $1.5 \times 10^6$ to $1.5 \times 10^8$, and even more particularly, about $1.5 \times 10^7$ units per milligram of total protein.

The TNF(LuKII) of the invention can contain chemically bound carbohydrate moieties, for example, glycosyl groups.

As described above, the inventive TNF(LuKII) comprises a plurality of protein fractions, e.g., at least three of and as many as seven or perhaps even more fractions which it is believed will have TNF activity. No matter how many fractions are obtained, each such protein fraction constituting the TNF(LuKII) is disruptable upon contact with enzymes such as trypsin or chymotrypsin to produce tryptic or chymotrypic digested proteins. At least one such protein fragment generated by enzyme digestion of each given protein fraction and at least one fragment generated by digestion of any other protein fraction or fractions, migrate to the same position following two dimensional analysis on a cellulose coated glass plate. Fragments generated following enzyme digestion of 70K and 25K proteins, for example, migrate to the same position on two dimensional peptide mapping analysis and are thus, related. In particular, two of the fragments generated by trypsin digestion of the 70K protein and two of the fragments generated by digestion of the 25K protein migrate to the same position upon two dimensional peptide mapping analysis, i.e., peptide homology. Peptide mapping analysis also shows that the 43K, 25K, 23K, 21K and 19K proteins, for example, are related, as are the 80K and 70K proteins.

In accordance with another aspect of the invention, several protein fractions of the inventive TNF(LuKII), having a different molecular weight, are recognized by monoclohal antibodies of the invention, produced by hybridomas, for example, ATCC HB 8887, deposited on Aug. 14, 1985.

In accordance with another aspect of the invention, the TNF(LuKII), which has a specific activity of $1.5 \times 10^5$ to $1.5 \times 10^8$ units per milligram of total protein, is in vitro cytotoxic or cytostatic, or has no effect on various human tumor cell lines.

For example, cytotoxic effects of hTNF on the following cell lines have been shown: SK-MG-4 (astrocytoma), MCF-7 (breast cancer), BT-20 (breast cancer), SK-BR-3 (breast cancer), ME-180 (cervix cancer), SK-CO-1 (colon cancer) and RPMI 7931 (melanoma).

Cytostatic effects of hTNF on the following cell lines, for example, have also been shown: SK-LU-1 (lung cancer), RPMI 4445 (melanoma), SK-MEL-29 (melanoma), SK-MEL-109 (melanoma) and SK-OV-3 (ovary cancer).

The present invention also concerns a method of producing monoclonal antibodies against TNF(LuKII) by propagating a hybridoma cell line which secretes such monoclonal antibody and harvesting secreted antibody.

Another aspect of the invention relates to a method of assaying a sample for the presence of TNF(LuKII), which comprises contacting the sample with a monoclonal antibody against TNF(LuKII), separating the antibody with any TNF(LuKII) which has combined therewith, and assaying the separated antibody for the presence of any TNF(LuKII) combined therewith. For example, using monoclonal antibodies of the invention, both enzyme linked immunosorbent assays and radioimmunoassays, can be used to detect the presence of TNF(LuKII) in a sample.

Two particular methods of assaying a sample for the presence of TNF(LuKII) are as follows:

(1) Competitive Method

An antibody, e.g., a monoclonal antibody, having an affinity to TNF(LuKII) is coated on a substrate, e.g., glass beads. Such coated beads are contacted with an unknown sample suspected of containing TNF(LuKII). Labelled TNF, e.g., radiolabelled or enzyme labelled, is allowed to contact the coated bead and unknown sample. Washing is then conducted. The amount of labelled TNF(LuKII) that binds is effected by any TNF(LuKII) in the unknown sample (unlabelled TNF(LuKII)). If there is no TNF(LuKII) in the sample, all the labelled TNF(LuKII) binds. The more TNF(LuKII) in the sample, the less labelled TNF(LuKII) binds. To determine the binding of the labelled TNF(LuKII), counts are taken if the label is a radiolabel and if an enzyme label is utilized, the enzymatic activity is determined.

(2) Non-Competitive Method

A substrate, e.g., polystyrene beads, is coated with an antibody, e.g., a monoclonal antibody having an affinity for TNF(LuKII). The coated beads are then contacted with an unknown sample suspected of containing TNF(LuKII). The bead is then washed and a labelled antibody having an affinity for TNF(LuKII) is then allowed to contact the bead. Washing is then conducted. The amount of antibody bound to the bead is a reflection of the TNF(LuKII) in the sample. If there is no TNF(LuKII) in the sample, there is no binding of the antibody. The more TNF(LuKII) in the sample, the greater the binding of the antibody. The TNF(LuKII) acts as a bridge between the labelled antibody and the unlabelled antibody.

The monoclonal antibodies of the invention can also be used to obtain the purified TNF(LuKII) of the invention. For example, a monoclonal antibody can be immobilized on a solid support, e.g., attached to Sepharose beads in a column, and the crude TNF(LuKII) passed through the column and the column washed with buffers. Immobilized TNF(LuKII) bound to the monoclonal antibody is then dissociated therefrom by using a dissociation buffer.

The invention also relates to the treatment of a patient having a tumor by administering to such patient a tumor-necrotic or a regression-effective amount of TNF(LuKII) of the invention, i.e., having a specific activity of at least $1.5 \times 10^5$ units per milligram of protein, more particularly, $1.5 \times 10^5$ to $1.5 \times 10^8$ units per milligram protein, more particularly, $1.5 \times 10^6$ to $1.5 \times 10^8$ and even more particularly, about $1.5 \times 10^7$ units per milligram of total protein.

DESCRIPTION OF THE DRAWINGS

The invention will be further described with reference to the accompanying drawings wherein:

FIGS. 5a and 5b are tryptic peptide maps of $^{125}$I-labeled proteins in purified TNF(LuKII). $^{125}$I-labeled TNF(LuKII) was fractionated on NaDodSO$_4$/PAGE and individual protein bands present in gel slices were incubated overnight in the presence of 50 μg/mL of L-1-tosylamido-2-phenylethyl chloromethyl ketone-(TPCK)-treated trypsin. The individual gel slices were then washed with water and 10,000 CPM samples of each lyophilized to dryness. These samples were dissolved in a buffer containing formic acid and acetic acid and applied to cellulose pre-coated glass TLC plates at the origin (x). Electrophoresis was performed from right to left followed by ascending chromatography in a buffer containing butanol, pyridine and acetic acid. Autoradiographs of the tryptic maps of the Mr 80,000, 70,000, 43,000, 25,000, 23,000, 21,000 and 19,000 proteins are presented in FIG. 5a. FIG. 5b shows tryptic maps of the Mr 25,000, 70,000 and a mixture of the 25,000 and 70,000 proteins.

FIGS. 6a and 6b are chymotryptic peptide maps of $^{125}$I-labeled proteins in purified TNF(LuKII). $^{125}$I-labeled proteins present in the purified TNF(LuKII) preparation were processed as described in FIG. 5, except that for this digestion, 50 μg/mL of N-α-tosyllysine chloromethyl keton(TLCK)-treated chymotrypsin was used. Autoradiographs of the chymotryptic maps of the Mr 80,000, 70,000, 43,000, 25,000, 23,000, 21,000 and 19,000 proteins are presented in FIG. 6a. FIG. 6b shows chymotryptic maps of the Mr 25,000, 70,000, and a mixture of the Mr 25,000 and 70,000 proteins.

FIG. 7 shows the results of immunoblotting analysis of TNF(LuKII) with T1-18 mouse monoclonal antibody. A sample of TNF(LuKII) containing 10,000 units of TNF(LuKII) was fractionated by NaDodSO$_4$/PAGE. Fractionated proteins were transferred to a nitrocellulose membrane and processed.

The invention will be further described in the following illustrative non-limiting examples wherein all parts are by weight unless otherwise expressed.

DETAILED DESCRIPTION OF INVENTION

Examples

Example 1

Production of Tumor Necrosis Factor

LuKII cells (a cell line of B-cell origin) were obtained as described in Pickering., L. A., Kronenberg, L. H. & Stewart, W. E., II, *Proc. Natl. Acad. Sci U.S.A.*, 77, 5938–5942 (1980), and were cultured in the following manner in order to obtain human tumor necrosis factor produced by the LuKII cells [i.e., TNF(LuKII)]:

LuKII cells ($8 \times 10^5$ cells/ml) were placed in RPMI 1640 media containing 8% fetal calf serum (FCS) with 10 ng/ml of mezerein (L.C. Services, Woburn, Mass.) for 48 hours. The cells were then removed from the media by centrifugation, resuspended in fresh RPMI 1640 media lacking any protein supplement and allowed to incubate for an additional 48 hours. Cells were removed by centrifugation, and the culture media used as the source of TNF(LuKII).

Example 2

Purification of TNF(LuKII)

Figure 1:
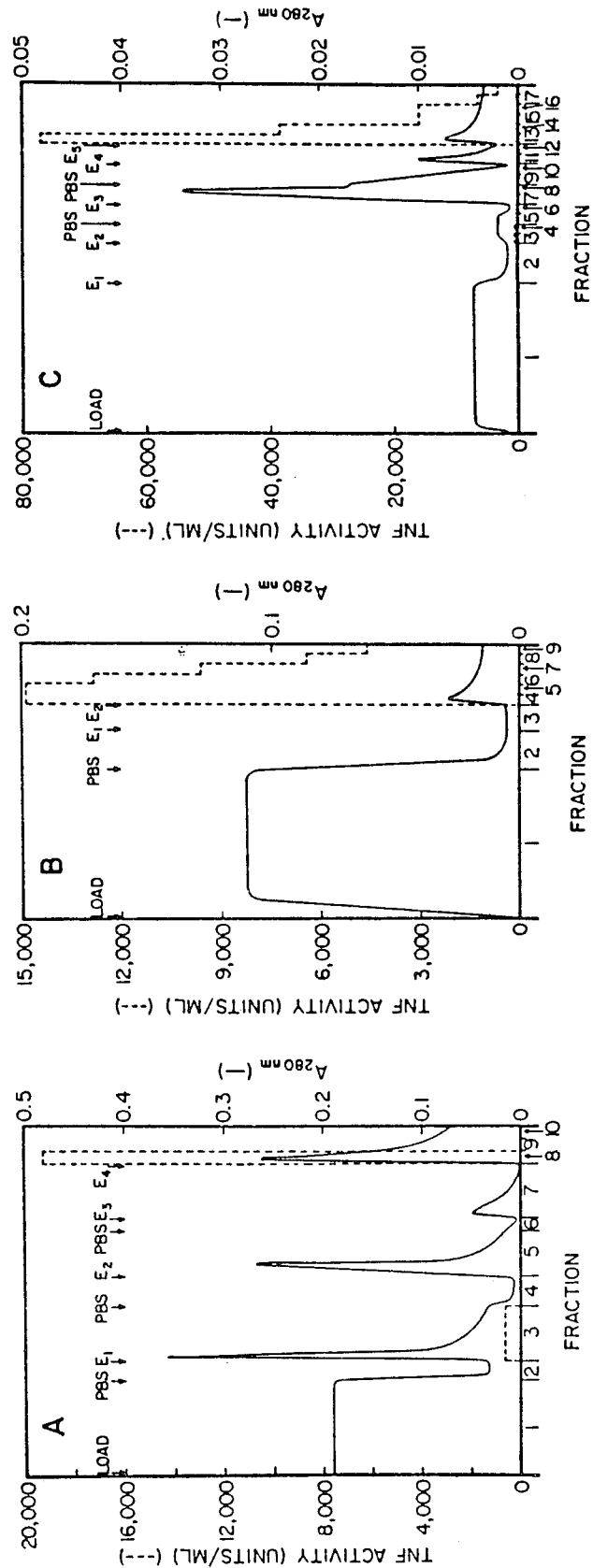
FIG. 1a is a chromatograph of media conditioned by the LuKII cell line, containing TNF(LuKII), on a controlled pore glass column. LuKII culture media (8 liters) containing 200 units/mL of TNF(LuKII) was applied to a controlled pore glass column (50 mL) equilibrated with phosphate buffered saline (20 mM sodium phosphate, pH 7.0, 0.15M NaCl) (PBS). The column was washed with the following buffers in sequence: PBS (75 mL), PBS containing 20% ethylene glycol (v/v) ($E_1$) (225 mL), PBS (120 mL), 20 mM sodium phosphate, pH 7.0, containing 1.15 M NaCl (PBS+1M NaCL) ($E_2$) (175 mL), PBS (50 mL), 5 mM sodium phosphate, pH 6.8, ($E_3$) (225 mL), and 5 mM sodium phosphate, pH 6.8, containing 5% triethylamine (v/v) ($E_4$) (150 mL). Eluted fractions were collected in polypropylene bottles. The material eluted with the $E_4$ buffer was collected in 50 mL aliquots.
FIG. 1b is a lentil lectin Sepharose column chromatograph of TNF(LuKII) purified by controlled pore glass chromatography. 150 mL of the partially purified TNF(LuKII) eluted from the controlled pore glass column was loaded onto a lentil lectin sepharose column (10 mL) equilibrated with PBS. The column was washed sequentially with PBS (40 mL), PBS+1M NaCl ($E_1$) (24 mL), and PBS+1M NaCl containing 0.2M α-methyl-D-mannoside ($E_2$) (60 mL). The material eluted with the α-methyl-D-mannoside containing buffer was collected in 10 mL aliquots.
FIG. 1c is a procion red agarose column chromatograph of the TNF(LuKII) purified sequentially first on a controlled pore glass column and then on a lentil lectin sepharose column. 60 mL of partially purified TNF(LuKII) eluted from the lentil lectin column was diluted 1:1 with PBS and loaded onto a procion red agarose column (4 mL) equilibrated with 20 mM sodium phosphate, pH 6.8, 0.65M NaCl (PBS+0.5M NaCl). The column was washed with the following buffers in sequence: PBS+0.5M NaCl ($E_1$) (30 mL), PBS+1M NaCl ($E_2$) (8 mL), PBS (8mL), PBS containing 50% ethylene glycol (v/v) ($E_3$) (8 mL), PBS (8mL), 0.1M Tris-HCl, pH 9.4+0.1M NaCl ($E_4$) (8 mL), and 0.1M Tris-HCl, pH 9.4+0.1M arginine ($E_5$) (24 mL). The material eluted with the 0.1M Tris-HCl, pH 9.4+0.1M arginine buffer was collected in 4 mL aliquots.

Human TNF(LuKII) was purified sequentially using controlled pore glass, lentil lectin Sepharose and procion red agarose column chromatography as follows (all affinity chromatography procedures were carried out at room temperature and all column fractions were collected in polypropylene tubes or bottles):

The TNF(LuKII) culture fluid was applied to a column of controlled pore glass-350 (Electronucleonics, Fairfield, N.J.) which bound all of the TNF activity. The column was washed with several buffers in sequence (as described in the legend to FIG. 1a) and then the TNF activity was eluted with a 5 mM sodium phosphate buffer, pH 6.8, containing 5% triethylamine (FIG. 1a). The eluted TNF was then applied to a lentil lectin Sepharose column (Pharmacia, Piscataway, N.J.), which was then washed first with phosphate buffered saline (PBS) followed by a 0.02M sodium phosphate buffer, pH 6.8, containing 1.15M NaCl (PBS+1M NaCl). TNF activity was then eluted from this column with PBS+1M NaCl buffer containing 0.2M α-methyl-D-mannoside (FIG. 1b). All TNF activity bound to the lentil lectin Sepharose column and 39% of the activity was recovered in the α-methyl-D-mannoside-containing buffer. The further washing of the column with the above buffer containing 50% ethylene glycol eluted only a small amount of TNF activity TNF from the lentil lectin column was then diluted 1:1 with PBS and loaded onto a procion red agarose column (Bethesda Research Laboratory, Bethesda, Md.). The column was washed sequentially with several buffers (as described in the legend to FIG. 1c) which removed protein having no TNF activity. The column was then washed with 0.1M tris-HCl, pH 9.4, containing 0.1M arginine. The TNF activity was eluted with this buffer, yielding TNF with a specific activity of $1.5 \times 10^7$ units/mg of protein. Table 1 summarizes the purification scheme for TNF(LuKII) with specific activities of the resulting fractions.

TABLE I

Purification of TNF(LuKII)

| Column | Load (units) | Load (Specific Activity) μ/mg | Recovery (units) | Recovery (Specific Activity) μ/mg | % Recovery | Fold Purification |
|---|---|---|---|---|---|---|
| Controlled Pore Glass | $1.6 \times 10^6$ | $5.3 \times 10^3$ | $9.6 \times 10^5$ | $3.8 \times 10^5$ | 60% | 72X |
| Lentil Lectin Sepharose | $9.6 \times 10^5$ | $3.8 \times 10^5$ | $6.3 \times 10^5$ | $1.3 \times 10^6$ | 39% | 245X |
| Procion Red Agarose | $6.3 \times 10^5$ | $1 \times 10^6$ | $6.3 \times 10^5$ | $1.5 \times 10^7$ | 39% | 2830X |

Example 3

Preparation of Monoclonal Antibody to TNF(LuKII)

BALB/c mice were injected with 1600 units of purified TNF(LuKII), with a specific activity of $1.5 \times 10^7$ units/mg. For the initial injection, TNF(LuKII) was mixed with Freund's complete adjuvant (1:1) and injected subcutaneously. Subsequent injections were given intraperitoneally in the absence of adjuvant. Serum antibody to TNF(LuKII) was determined by an enzyme linked immunosorbent assay (ELISA) in which the TNF(LuKII) was bound to polystyrene plates. After nine immunizations over a period of seven months, the spleen of one mouse with a high titer antibody directed against TNF(LuKII) was removed and fused with cells of the $P_3U_1$ mouse plasmacytoma cell line Resulting clones were screened for their ability to bind TNF(LuKII) in ELISA assays. A hybridoma (designated T1-18) producing antibody reactive with TNF(LuKII) was isolated and subcloned. This hybridoma grown in tissue culture media as well as in ascites served as a source of TNF(LuKII) antibody. The hybridoma has been deposited with the ATCC as HB 8887, deposited on Aug. 14, 1985.

Example 4

Biochemical Characterization of Purified TNF(LuKII)

Figure 2:
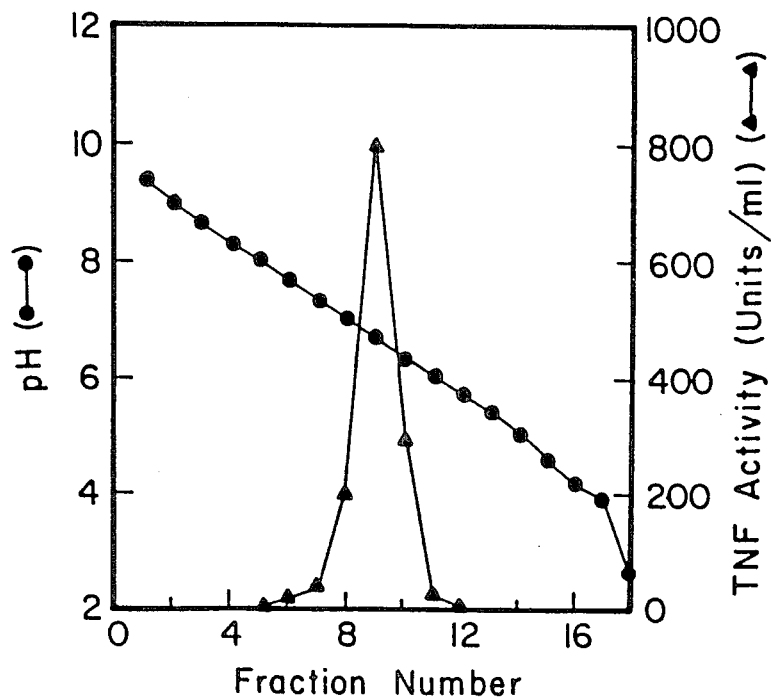
FIG. 2 is a graph indicating the isoelectric point of TNF(LuKII). A 60 μL sample of purified TNF(LuKII) containing 1500 units was applied to a pH 3.5–9.5 ampholine gel.

To initiate the characterization of the purified TNF(LuKII), isoelectrofocusing was performed using Ampholine Pagplates (pH 3.5 to 9.5) LKB Instruments, Gaitherburg, Md.). The gels were run at 30 watts for 1.5, hours at which time the pH gradient was measured. Human TNF was found to have an isoelectric point of approximately 6.7 (see FIG. 2). The gel was sliced into 18 equal pieces. The gel fractions were incubated for 18 hours in Eagle's Minimum Essential Medium (MEM) containing 10% fetal calf serum, and fractions were assayed for the presence of TNF(LuKII) in vitro.

Purified TNF(LuKII) was tested and was observed to cause hemorrhagic necrosis of the Meth A mouse sarcoma in the standard in vivo TNF assay. The in vivo TNF assay was performed as described (Williamson B. D. et al, supra). Essentially, (BALB/c×C57BL/6)F₁ female mice were injected intradermally with $5 \times 10^5$ Meth A BALB/c' sarcoma cells. After 7 days (tumor size approximately 7 mm average diameter), mice received either a single intravenous or intratumoral injection of the TNF(LuKII) preparation. After 24 hours, tumor hemorrhagic necrosis was scored according to Carswell et al, supra. TNF(LuKII) causes hemorrhagic necrosis of Meth A sarcoma after intraturmoral or intravenous injection and total tumor regression has been observed in some treated mice.

The in vitro assay for TNF was performed in 96-well microtiter plates. Serially diluted fractions were sterilized by ultraviolet radiation and the TNF-sensitive L cells (for example, derived from mouse L cells obtained from American Type Culture Collection) were added to each well at a density of $2 \times 10^4$ cells/well in 100 µL. After two days at 37° C., the plates were examined by phase-contrast microscopy and the percentage of dead cells was determined. The unitage of the samlle was calculated as the reciprocal of the highest dilution that killed 50% of the cells. All TNF assays were run in parallel with a laboratory standard and titers are expressed in laboratory units.

Purified TNF(LuKII) was iodinated as follows:

TNF(LuKII) was labeled with $^{125}$I using 1,3,4,6-tetrachloro-3α, 6α-diphenylglycouril (Iodo-gen, Pierce Chemical Co., Rockford, Ill.) as follows. Polypropylene tubes were coated with 100 µg of Iodo-gen (dissolved in chloroform) by evaporation of the solvent. A 2 ml sample of TNF(LuKII) (50,000 units/ml) with a specific activity of $1.5 \times 10^7$ units/mg of protein was incubated for 25 minutes at room temperature in an Iodo-gen coated tube containing 2 mCi of $^{125}$I. The labeled protein was then separated from the unbound $^{125}$I using a P-4 column (Bio-Rad, Richmond, Calif.) equilibrated with phosphate buffered saline (PBS) containing 50 µg/mL of cytochrome-C. The iodinated material eluted in the void volume of the column was divided into aliquots and stored at −80° C.

Following iodination, the radioactively labelled proteins present in the preparations were analyzed by NaDodSO$_4$/polyacrylamide gel electrophoresie (PAGE) which was performed in 18 cm slab gels according to conditions described by Laemmli, U.K. (1970), *Nature* (London), 227, 680–685.

All protein determinations were made using the Bio-Rad dye reagent (Bio-Rad, Richmond, Calif.), using bovine serum albumin as a standard.

Figure 3:
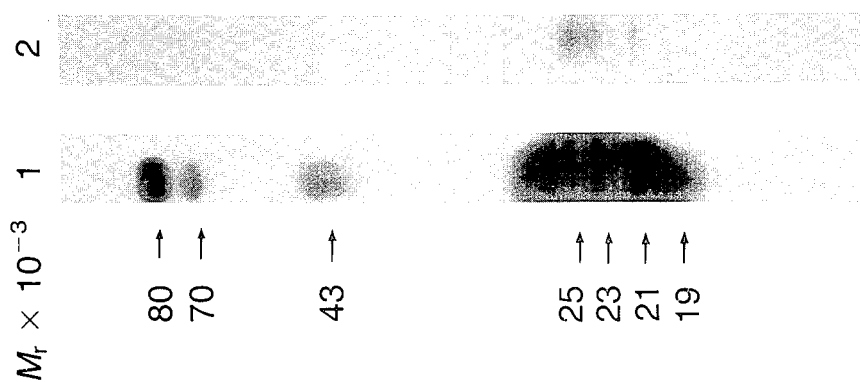
FIG. 3 is an autoradiograph resulting from NaDodSO$_4$ polyacrylamide gel electrophoresis (PAGE) of purified $^{125}$I-labeled TNF(LuKII). TNF(LuKII) was iodinated and fractionated by NaDodSO$_4$/PAGE. Autoradiographs were developed for 18 hours (lane 1) and 0.5 hour (lane 2). The following proteins provided Mr markers: myosin (200,000), β-galactosidase (130,000), phosphorylase b (94,000), bovine serum albumin (67,000), ovalbumin (43,000), α-chymotrypsinogen (25,700), β-lactoglobulin (18,400), lysozyme (14,300) and cytochrome C (12,300).

As can be seen in FIG. 3, the purified preparation of TNF(LuKII) contained seven protein bands with molecular weights of 80,000, 70,000, 43,000, 25,000, 23,000, 21,000 and 19,000 daltons (80K, 70K, 43K, 25K, 23K, 21K, 19K). The same seven protein bands were observed when non-labeled purified TNF(LuKII) was fractionated by NaDodSO$_4$/PAGE and examined by the silver staining of the gel. The Mr 80,000 and 70,000 forms were eluted from the gels and re-analyzed by NaDodSO$_4$/PAGE. They migrated once again to the Mr 70,000–80,000 region and no smaller molecular weight components were observed. In further experiments, purified TNF(LuKII) was boiled in NaDodSO$_4$, urea and β-mercaptoethanol and the same characteristic seven bands were found.

In order to ascertain which of the protein bands present in the purified TNF(LuKII) preparations was responsible for TNF activity, parallel samples of purified TNF(LuKII), one $^{125}$I-labeled and one unlabeled, were treated with NaDodSO$_4$ (0.1%) and β-mercaptoethanol (0.1M) and then fractionated by NaDodSO$_4$/PAGE. Upon completion of the electrophoresis, the lane containing the unlabeled TNF(LuKII) was cut into 4.4 mm slices and the slices put into Eagle's minimal essential media (MEM) containing 10% fetal calf serum (FCS). The proteins were then eluted from each gel slice by overnight incubation at 4° C. in MEM containing FCS. The samples were assayed for the presence of TNF as described above.

Figure 4:
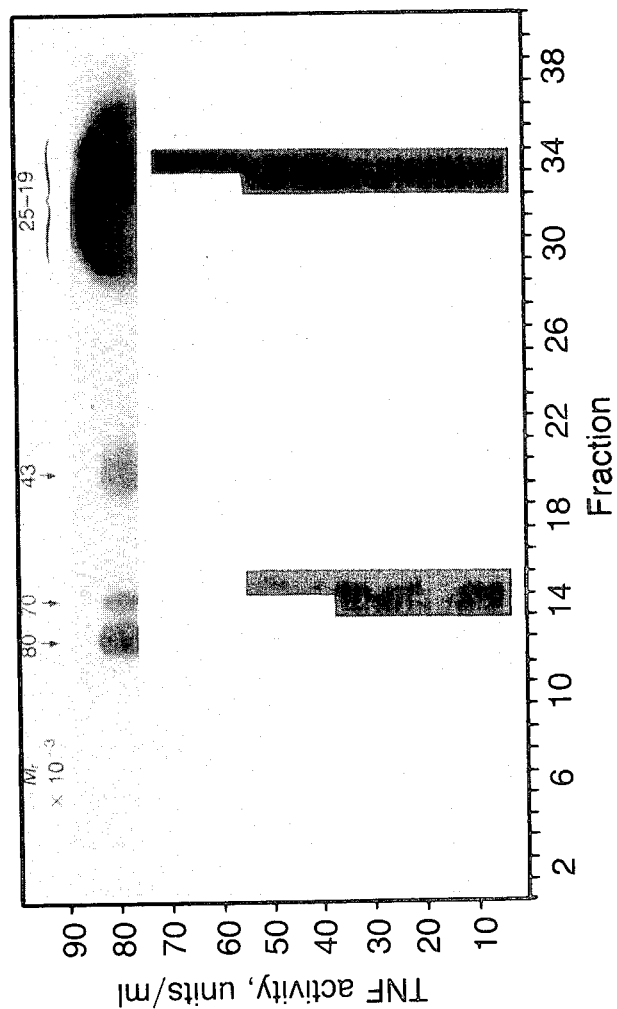
FIG. 4 is a graph showing recovery of TNF(LuKII) activity after NaDodSO$_4$/PAGE fractionation of TNF(LuKII). A sample of TNF(LuKII) containing 6000 units adjusted to contain 0.1% NaDodSO$_4$ and 0.1M β-mercaptoethanol was applied to a 12% polyacrylamide gel. Following electrophoresis, the gel was sliced and activity eluted and assayed. In an adjacent track, $^{125}$I-labeled TNF(LuKII) was fractionated and autoradiographed to determine the Mr of the TNF(LuKII) active fractions.

The parallel lane containing $^{125}$I-labeled TNF(LuKII) was dried immediately following the completion of the electrophoresis and the protein bands located by autoradiography. As can be seen in FIG. 4, TNF activity was recovered from the gel at molecular weights of approximately 70,000 and 19,000 to 25,000 daltons, corresponding to $^{125}$I-labeled protein bands at these positions. In experiments in which β-mercaptoethanol was not added to the TNF(LuKII) sample before NaDodSO$_4$/PAGE, TNF activity was also recovered at the 70,000 and 19,000 to 25,000 molecular weight range.

Since it was observed that following NaDodSO$_4$/PAGE, TNF activity was recovered at the 70,000 as well as the 19,000 to 25,000 dalton region, the relatedness of the various proteins present in the purified TNF(LuKII) preparations was then examined. To accomplish this, two dimensional chymotryptic and tryptic peptide mapping analyses of the individual protein bands present in the most purified TNF(LuKII) preparations were performed.

To perform the peptide mapping, an $^{125}$I-labeled preparation of purified TNF(LuKII) was fractionated by NaDodSO$_4$/PAGE and individual bands (i.e., 80K, 70K, 43K, 25K, 23K, 21K, 19K) localized by autoradiography were cut from the gel and treated with either TPCK treated trypsin or TLCK treated chymotrypsin. Digested fractions were then analyzed according to the methods of J. H. Elder et al, *Nature* (London), 267, 23–28 (1977).

Figure 5A:
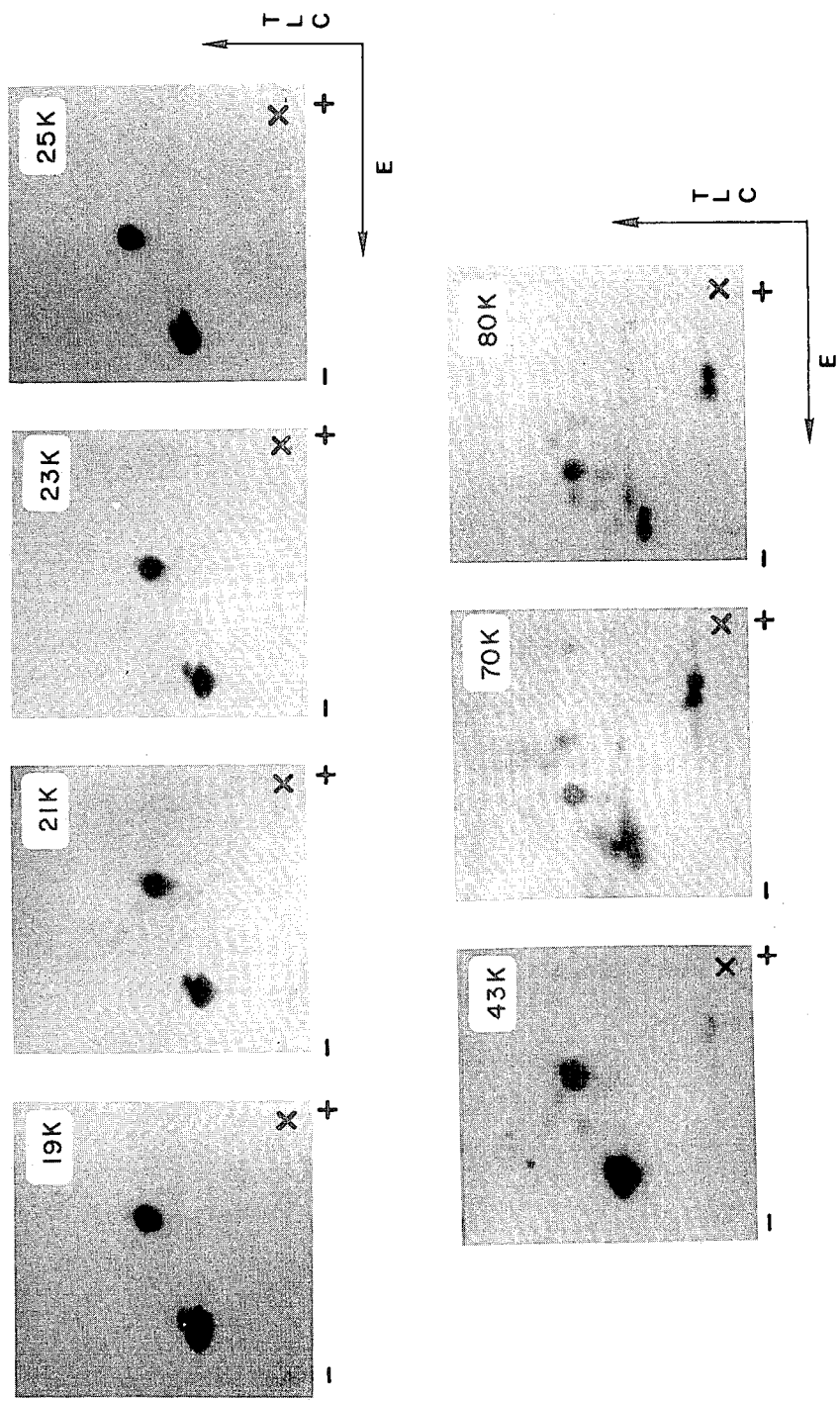
Figure 5B:
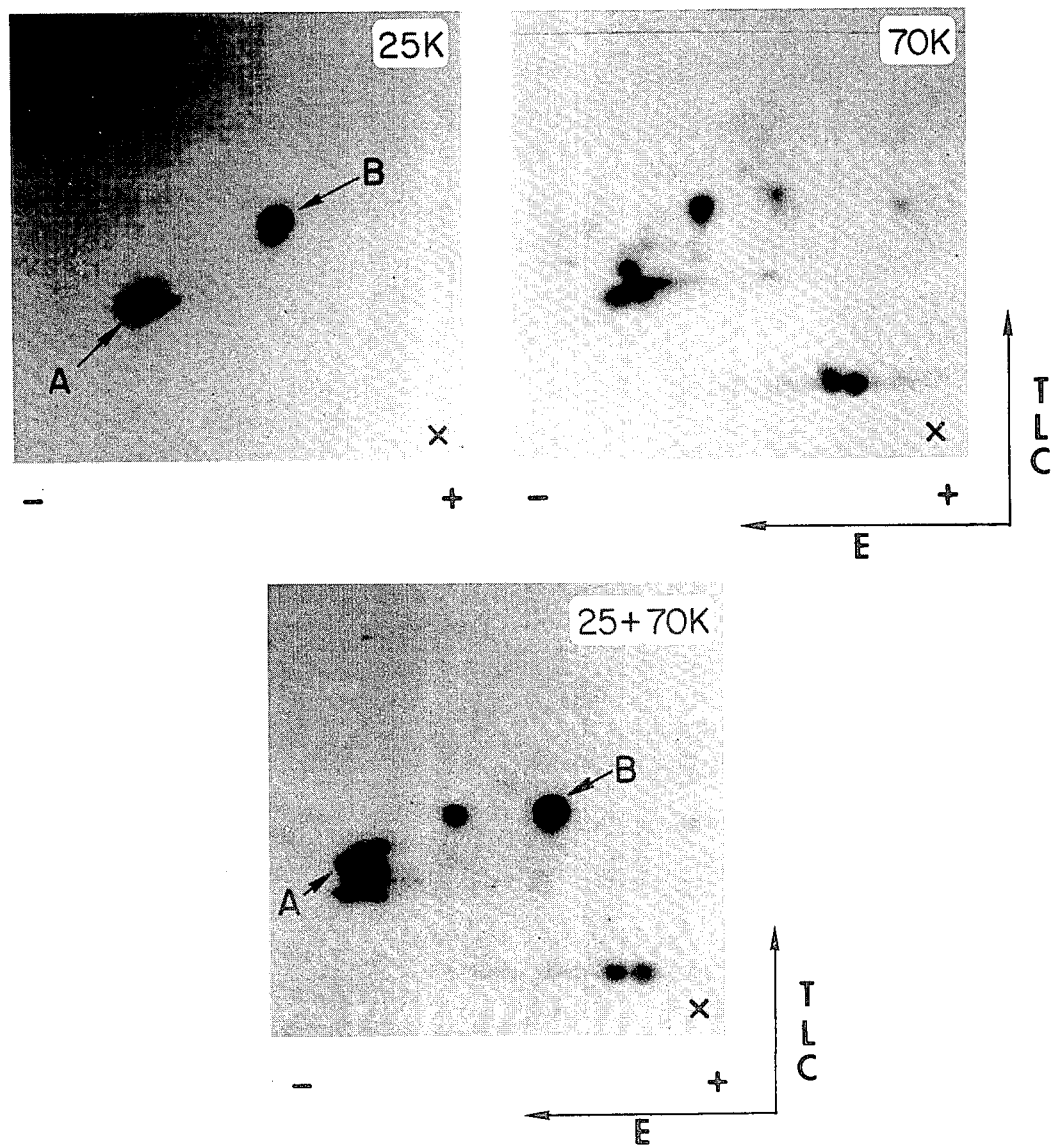
Figure 6A:
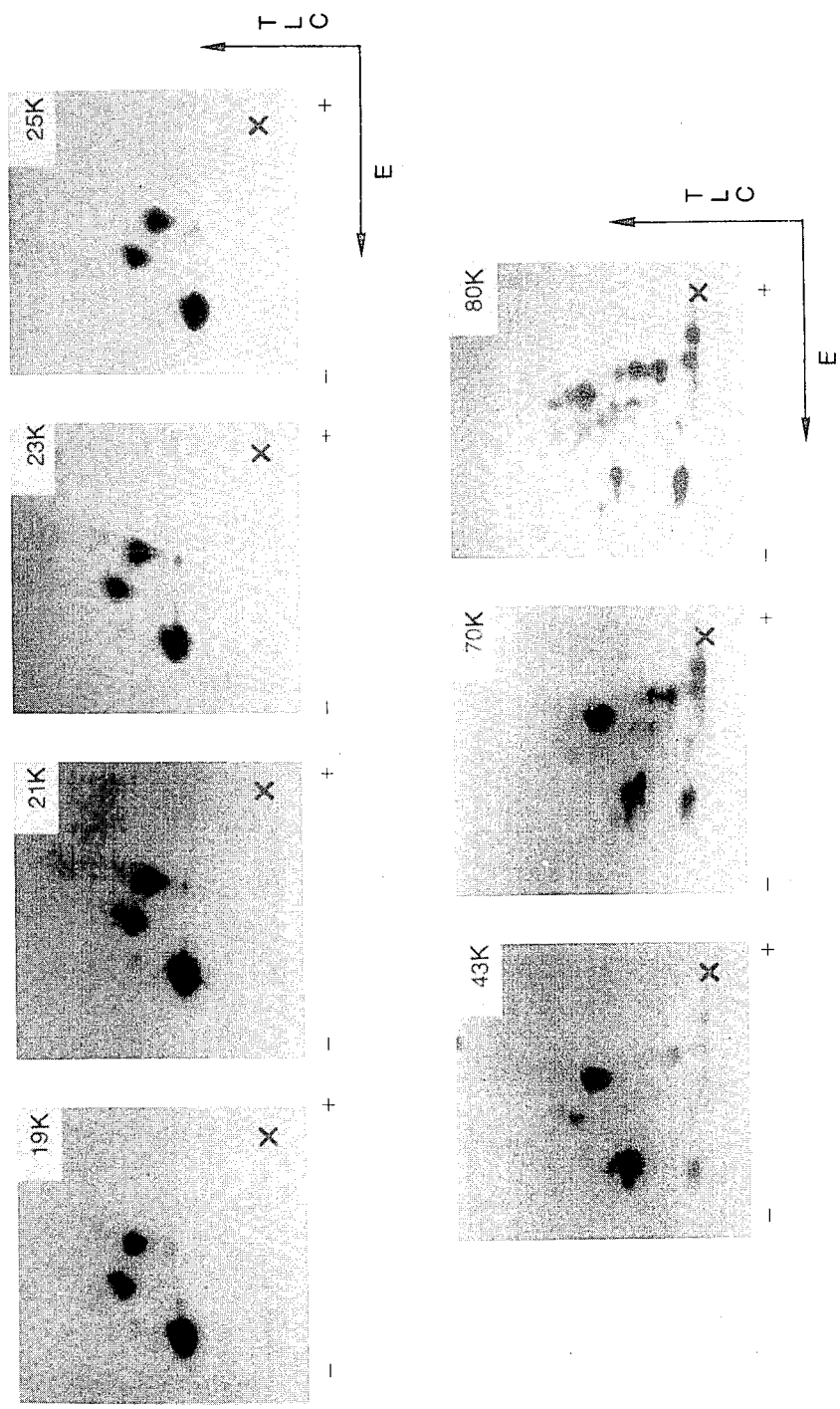

As seen in FIG. 5a, the tryptic peptide maps demonstrate that the 43K, 25K, 23K, 21K and 19K proteins are related and that the 80K and 70K proteins are related. To examine the relationship between the larger molecular weight proteins (e.g., 70K and 80K) and the smaller molecular weight proteins (e.g., 19 to 25K), tryptic digests of the 70K and 25K proteins were mixed so that they contained equal amounts of radioactivity and the mixture was analyzed by peptide mapping analysis. As seen in FIG. 5b, two of the fragments (termed A and B) generated by digestion of the 70K protein and two of the fragments generated by digestion of the 25K protein overlap, i.e., migrate to the same position upon peptide mapping analysis. A similar analysis was carried out using chymotrypsin as the proteolytic enzyme. As seen in FIG. 6a, the 43K, 25K, 23K, 21K and 19K proteins are related and the 80K and 70K proteins are related. To once again examine the relatedness between the smaller and larger molecular weight proteins, the chymotrypsin digests 25K and 70K proteins were mixed and the mixture analysed by peptide mapping analysis. As seen in FIG. 6b, at least three of the fragments generated (termed A, B and C) following chymotrypsin digestion of the 25K protein migrate to the same position as three of the fragments generated by digestion of the 70K protein.

Further evidence for the relationships among the various proteins in purified TNF(LuKII) comes from immunoblotting analyses with T1-18 monoclonal antibody to TNF(LuKII). Western blotting analysis was performed essentially as described in Burnette, W. N. (1981), *Anal. Biochem.*, 112, 195–203. Briefly, preparations of purified TNF(LuKII) were fractionated by NaDodSO$_4$/PAGE and the proteins present in the gel were transferred to nitrocellulose paper overnight at 100 mA. Following incubation of the nitrocellulose paper in a buffer containing bovine serum albumin (BSA), the nitrocellulose paper was exposed for two hours to 40 mL of T1-18 monoclonal antibody-containing culture medium. The nitrocellulose paper was then washed extensively and incubated overnight in 10 mM Tris-HCl, pH 7.4, +0.9% NaCl containing 5% BSA and $^{125}$I-labeled rabbit anti-mouse IgG. The nitrocellulose paper was further washed and exposed to X-ray film.

As seen in FIG. 7, exposure of this nitrocellulose paper to the X-ray film reveals that the monoclonal antibody to TNF(LuKII) reacts with proteins with molecular weights of 43K and 19K to 25K, thus showing shared determinants on the Mr 43,000 and 19–25,000 proteins. Antibody did not react with the higher molecular weight forms, even though these have been shown to be related to the Mr 43,000 and lower molecular weight components. This could be due to the inaccessability of the determinant on the Mr 70,000 and 80,000 species. Thus, analysis indicates that there are a number of structural related proteins in purified TNF(LuKII) and that TNF activity is associated with nondissociable high molecular weight and low molecular weight forms. It is concluded that the seven proteins in the purified TNF(LuKII) are the products of related genes or products of a single gene that undergoes extensive processing.

Thus, using peptide map analyses, and a monoclonal antibody to human TNF in western blotting analysis it has been demonstrated that the various molecular weight proteins present in the purified TNF(LuKII) preparations are related.

Example 5

The Relationship of Mouse TNF to TNF(LuKII)

A standard lot of partially purified mouse serum TNF with a specific activity of $2 \times 10^4$ units of TNF per mg of protein was used in these studies. A unit of TNF is defined as the amount of protein causing killing of 50% of the L cells in the standard in vitro TNF assay.

To investigate further the relationship of mouse TNF to TNF(LuKII), L cells were made resistant to TNF(LuKII) by repeated passage in TNF(LuKII)-containing medium. TNF(LuKII)-resistant cells showed complete cross-resistance to mouse TNF. L cell lines made resistant to mouse TNF or to partially purified TNF(LuKII) are resistant to purified TNF(LuKII). TNF(LuKII) is cytotoxic to mouse L cells sensitive to mouse TNF.

It will be appreciated that the instant specification and claims are set forth by way of illustration and not limitation, and that various modifications and changes may be made without departure from the spirit and scope of the present invention.

What is claimed is:

1. A process for producing human tumor necrosis factor produced by human cell line Luk II (TNF(LukII), said human TNF (LuKII) having a specific activity of at least $1.5 \times 10^5$ units per milligram of total protein and continuing chemically bound carbohydrate moieties, which process comprises contacting a TNF (LuKII)-containing protein composition, which has been harvested from human cell lines of hematopoietic origin or from recombinant origin, in separate adsorption stages with glass beads, lentil lectin bound to Sepharose, and procion red agarose, thereby selectively adsorbing TNF (LuKII) in each stage while leaving some impurities unadsorbed, each contact stage being followed by contacting the adsorbent with an eluant thereby to obtain a solution of more highly purified TNF (LuKII) after each stage.

2. A process according to claim 1, wherein the glass beads are the first stage adsorbent, the Sepharose bound lectin is the second stage adsorbent and the procion red agarose is the third stage adsorbent.

* * * * *